United States Patent
Grützmacher et al.

(10) Patent No.: US 7,112,696 B2
(45) Date of Patent: Sep. 26, 2006

(54) PREPARATION OF PHOSPHORUS COMPOUNDS

(75) Inventors: Hansjörg Grützmacher, Wettswil a.A. (CH); Elisabetta Piras, Zürich (CH)

(73) Assignee: Bayer Chemicals AG, Leverkusen (DE)

( * ) Notice: Subject to any disclaimer, the term of this patent is extended or adjusted under 35 U.S.C. 154(b) by 336 days.

(21) Appl. No.: 10/839,652

(22) Filed: May 5, 2004

(65) Prior Publication Data

US 2005/0020835 A1 Jan. 27, 2005

(30) Foreign Application Priority Data

May 7, 2003 (DE) ................................ 103 20 261

(51) Int. Cl.
*C07F 9/50* (2006.01)
*C07F 9/53* (2006.01)

(52) U.S. Cl. ................................ 568/8; 568/12; 568/14

(58) Field of Classification Search .................... 568/8, 568/12, 14

See application file for complete search history.

(56) References Cited

U.S. PATENT DOCUMENTS 4,514,575 A 4/1985 Lee et al. ...................... 568/17

FOREIGN PATENT DOCUMENTS

WO 03/048175 6/2003

OTHER PUBLICATIONS

Deblon S et al: "Highly Distorted $D^8$-Rhodium (+1) and $D^{10}$-Rhodium (−1) Complexes: Synthesis, Reactivity, and Structures in Solution and Solid State" New Journal of Chemistry, CNRS-Gauthier-Villars, Montrouge, FR, Bd 25, Nr. 1, 2001 Seiten 83-92, XP008015055 ISSN: 1144-0546 "das ganze Dokument".

Thomaier J et al: "Dibenzotropylidene Phosphanes (Tropps): Synthesis and Coinage Metal Complexes" New Journal of Chemistry, CNRS-Gauthier-Villars, Montrouge, FR, Bd. 22, Nr. 9, 1998, Seiten 947-958, XP008015151 ISSN: 1144-0546 "das ganze Dokument".

Demay S et al: "Stereoselective Preparation of Phosphine Oxides via a 2,3-Sigmatropic Shift of Allylic Diphenylphosphinites" Tetrahedron Letters, Elsevier Science Publishers, Amsterdam, NL, Bd. 40, Nr. 27, Jul. 2, 1999, Seiten 4981-4984, XP004169375 ISSN: 0040-4039 "Beispiele 1-3; Tabelle 1".

*Primary Examiner*—Bernard Dentz
(74) *Attorney, Agent, or Firm*—Jennifer R. Seng

(57) ABSTRACT

The present invention relates to a process for preparing phosphorus compounds and intermediates.

20 Claims, No Drawings

PREPARATION OF PHOSPHORUS COMPOUNDS

BACKGROUND OF THE INVENTION

1. Field of the Invention

The present invention relates to a process for preparing phosphorus compounds and intermediates.

2. Brief Description of the Prior Art

Deblon (Thesis No. 13920, ETH Zurich, 2000) and Maire (Thesis No. 14396, ETH Zurich, 2001) disclose that transition metal complexes of olefin-phosphine compounds are particularly suitable for homogeneous catalytic reactions, especially hydrogenations and hydrosilylations. Typically, they are prepared by using secondary phosphines (see also Thomaier et al., New. J. Chem. 1998, 947–958 and Deblon et al., New. J. Chem. 2001, 25, 83–92), which is unsatisfactory for industrial use due to their spontaneous combustibility and associated safety requirements.

There is therefore a need to develop a process for preparing olefin-phosphine compounds which does not require the use of secondary phosphines.

SUMMARY OF THE INVENTION

Surprisingly, a process has now been found for preparing compounds of the formula (I)

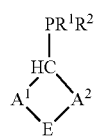

(I)

in which $R^1$ and $R^2$ are each independently a monovalent radical which in each case has 1 to 30 carbon atoms or $PR^1R^2$ as a whole is a 5- to 9-membered heterocyclic radical which contains a total of 2 to 50 carbon atoms and may contain up to three further heteroatoms which are selected from the group of oxygen and nitrogen, and $A^1$ and $A^2$ are each independently a substituted or unsubstituted ortho-arylene radical and E is $E^1$ or $E^2$ where $E^1$ is an unsubstituted, monosubstituted or disubstituted vicinal cis-alkenediyl radical and $E^2$ is a vicinal alkanediyl radical in which the two yl carbon atoms each bear one or two hydrogen atoms, which is characterized in that in a step a)

compounds of the formula (II)

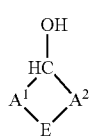

(II)

in which $A^1$, $A^2$ and E are each as defined above are converted by reacting with compounds of the formula (III)

$R^1R^2P\text{-Hal}$ (III)

in which $R^1$ and $R^2$ are each as defined above and $Hal^1$ is chlorine, bromine or iodine, preferably chlorine, in the presence of acid or base, to compounds of the formula (IV)

(IV)

in which $A^1$, $A^2$, E, $R^1$ and $R^2$ are each as defined above and in a step b), the compounds of the formula (IV) are converted to compounds of the formula (I) by reduction.

The compounds of formulae (I) and (IV) also encompass in particular chiral compounds. These may occur in various stereoisomeric forms which behave either as image and mirror image (enantiomers) or do not behave as image and mirror image (diastereomers). The process according to the invention is suitable both for the preparation of stereoisomerically pure forms of the particular compound or any mixtures of the stereoisomers, for example racemates or diastereomer pairs.

In the context of the invention, the terms stereoisomerically enriched (enantiomerically enriched or diastereomerically enriched) mean stereoisomerically pure (enantiomerically pure or diastereomerically pure) compounds or mixtures of stereoisomers (enantiomers or diastereomers) in which one stereoisomer (enantiomer or diastereomer) is present in a greater fraction than another or the other. Stereoisomerically enriched means, for example and with preference, a content of one stereoisomer of 50% to 100% by weight, more preferably 70% to 100% by weight and most preferably 90 to 100% by weight, based on the sum of the stereoisomers.

In one embodiment of the process according to the invention, in the case of the presence of stereoisomer mixtures of compounds of the formula (IV), these may be separated in a manner known per se.

In the case of diastereomer mixtures, the separation may be effected, for example, by chromatography or by fractional crystallization, in the case of enantiomer mixtures, for example, by fractional crystallization in the presence of an enantiomerically enriched auxiliary reagent or by chromatography on an at least enantiomerically enriched column material.

In a further embodiment, the stability of the phosphorus-oxygen bond may also be used to convert at least one of the $R^1$, $R^2$, $A^1$, $A^2$ and E radicals in the compounds of the formula (IV) by chemical transformations known per se to another $R^1$, $R^2$, $A^1$, $A^2$ and E radical. Chemical transformations known per se are, for example, customary transformations of functional groups or functionalizations, as described in J. March, Advanced Organic Chemistry, Wiley, 1992.

In the context of the invention, all radical definitions, parameters and illustrations hereinabove and listed hereinbelow, mentioned generally or within areas of preference, i.e. the particular areas and areas of preference, may be combined as desired.

DETAILED DESCRIPTION OF THE INVENTION

In the context of the invention, aryl as a substituent is, for example, carbocyclic aromatic radicals having 6 to 24 skeleton carbon atoms, for example preferably phenyl, naphthyl, phenanthrenyl and anthracenyl, or heteroaromatic radicals having 5 to 24 skeleton carbon atoms in which no, one, two or three skeleton carbon atoms per cycle, but at least one skeleton carbon atom in the entire molecule, are substituted by heteroatoms which are selected from the group of nitrogen, sulphur and oxygen. They are, for example, preferably pyridinyl, oxazolyl, thiophenyl, benzofuranyl, benzothiophenyl, dibenzofuranyl, dibenzothiophenyl, furanyl, indolyl, pyridazinyl, pyrazinyl, imidazolyl, pyrimidinyl and quinolinyl. In the context of the invention, specifications such as $C_5$ in the case of aryl radicals relates to the sum of the carbon atoms and heteroatoms of the aromatic skeleton.

Moreover, the carbocyclic aromatic radicals or heteroaromatic radicals may be substituted by up to five identical or different substituents per cycle. For example and with preference, the substituents are selected from the group of bromine, fluorine, chlorine, nitro, cyano, free and protected formyl, free and protected hydroxyl, $C_1$–$C_{12}$-alkyl, $C_1$–$C_{12}$-haloalkyl, $C_1$–$C_{12}$-alkoxy, $C_1$–$C_{12}$-haloalkoxy, $C_5$–$C_{14}$-aryl, for example phenyl, $C_6$–$C_{15}$-arylalkyl, for example benzyl, di($C_1$–$C_{12}$-alkyl)amino, ($C_1$–$C_{12}$-alkyl)amino, CO($C_1$–$C_{12}$-alkyl), OCO($C_1$–$C_{12}$-alkyl), NHCO($C_1$–$C_{12}$-alkyl), N($C_1$–$C_6$-alkyl)CO($C_1$–$C_{12}$-alkyl), CO($C_5$–$C_{14}$-aryl), OCO($C_5$–$C_{14}$-aryl), NHCO($C_5$–$C_{14}$-aryl), N($C_1$–$C_6$-alkyl)CO($C_5$–$C_{14}$-aryl), COO—($C_1$–$C_{12}$-alkyl), COO—($C_5$–$C_{14}$-aryl), CON($C_1$–$C_{12}$-alkyl)$_2$ or CONH($C_1$–$C_{12}$-alkyl), $CO_2M$, $CONH_2$, $SO_2NH_2$, $SO_2N$($C_1$–$C_{12}$-alkyl)$_2$, $SO_3M$ where M is in each case optionally substituted ammonium, lithium, sodium, potassium or caesium.

For example and with preference, aryl is phenyl, naphthyl, pyridinyl and quinolinyl, each of which may be further substituted by no, one, two or three radicals per cycle by radicals which are selected from the group of fluorine, chlorine, cyano, $C_1$–$C_8$-alkyl, $C_1$–$C_6$-perfluoroalkyl, $C_1$–$C_6$-alkoxy, phenyl, benzyl, di($C_1$–$C_{12}$-alkyl)amino, CO($C_1$–$C_{12}$-alkyl), COO—($C_1$–$C_{12}$-alkyl), CON($C_1$–$C_{12}$-alkyl)$_2$ and $SO_2N$($C_1$–$C_{12}$-alkyl)$_2$.

More preferably, aryl is phenyl or naphthyl, each of which may be substituted by no, one, two or three radicals per cycle by radicals which are selected from the group of fluorine, chlorine, cyano, $C_1$–$C_6$-alkyl, $C_1$–$C_6$-perfluoroalkyl, $C_1$–$C_8$-alkoxy, phenyl and $SO_2N$($C_1$–$C_{12}$-alkyl)$_2$.

In the context of the invention, the definition and the areas of preference also apply similarly to aryloxy substituents and the aryl moiety of an arylalkyl radical. Protected formyl means a formyl radical which is protected by conversion to an aminal, acetal or a mixed aminal acetal, and aminals, acetals and mixed aminal acetals may be acyclic or cyclic.

For example and with preference, protected formyl is a 1,1-(2,4-dioxycyclopentanediyl) radical.

Protected hydroxy is a hydroxyl radical which is protected by conversion to a ketal, acetal or a mixed aminal acetal, and the acetals and mixed aminal acetals may be acyclic or cyclic.

For example and with preference, protected hydroxyl is a tetrahydropyranyl radical (THP).

In the context of the invention, alkyl, alkylene, alkoxy and alkenyl are in each case independently a straight-chain, cyclic, branched or unbranched alkyl, alkylene, alkenyl and alkoxy radical respectively, each of which may be further substituted by $C_1$–$C_4$-alkoxy in such a way that each carbon atom of the alkyl, alkylene, alkoxy or alkenyl radical bears at most one heteroatom selected from the group of oxygen, nitrogen and sulphur.

The same applies to the alkylene moiety of an arylalkyl radical.

In the context of the invention, $C_1$–$C_6$-alkyl is, for example, methyl, ethyl, 2-ethoxyethyl, n-propyl, isopropyl, n-butyl, tert-butyl, n-pentyl, cyclohexyl and n-hexyl, $C_1$–$C_8$-alkyl is additionally, for example, n-heptyl, n-octyl or isooctyl, $C_1$–$C_{12}$-alkyl is further additionally, for example, norbornyl, adamantyl, n-decyl and n-dodecyl, and $C_1$–$C_{18}$-alkyl is still further additionally n-hexadecyl and n-octadecyl.

In the context of the invention, $C_1$–$C_4$-alkylene is, for example, methylene, 1,1-ethylene, 1,2-ethylene, 1,1-propylene, 1,2-propylene, 1,3-propylene, 1,1-butylene, 1,2-butylene, 2,3-butylene and 1,4-butylene, and $C_1$–$C_8$-alkylene is additionally 1,5-pentylene, 1,6-hexylene, 1,1-cyclohexylene, 1,4-cyclohexylene, 1,2-cyclohexylene and 1,8-octylene.

In the context of the invention, $C_1$–$C_4$-alkoxy is, for example, methoxy, ethoxy, isopropoxy, n-propoxy, n-butoxy and tert-butoxy, and $C_1$–$C_8$-alkoxy is additionally cyclohexyloxy.

In the context of the invention, $C_2$–$C_8$-alkenyl is, for example, allyl, 3-propenyl and 4-butenyl.

Haloalkyl and haloalkoxy are in each case independently a straight-chain, cyclic, branched or unbranched alkyl and alkoxy radical respectively, each of which is singly, multiply or fully substituted by halogen atoms. Radicals which are fully substituted by fluorine are referred to as perfluoroalkyl and perfluoroalkoxy respectively.

In the context of the invention, $C_1$–$C_6$-haloalkyl is, for example, trifluoromethyl, 2,2,2-trifluoroethyl, chloromethyl, fluoromethyl, bromomethyl, 2-bromoethyl, 2-chloroethyl, nonafluorobutyl. $C_1$–$C_8$-haloalkyl is additionally, for example, n-perfluorooctyl, and $C_1$–$C_{12}$-haloalkyl is additionally, for example, n-perfluorododecyl.

In the context of the invention, $C_1$–$C_4$-haloalkoxy is, for example, trifluoromethoxy, 2,2,2-trifluoroethoxy, 2-chloroethoxy, heptafluoroisopropoxy, and $C_1$–$C_8$-haloalkoxy is additionally n-perfluorooctyloxy.

The preferred substitution patterns are defined hereinbelow:

$R^1$ and $R^2$ are preferably each independently $C_1$–$C_{18}$-alkyl, $C_3$–$C_{12}$-alkenyl, $C_1$–$C_{18}$-perfluoroalkyl, $C_1$–$C_{18}$-perfluoroalkoxy, $C_1$–$C_{18}$-alkoxy, $C_5$–$C_{24}$-aryl, $C_5$–$C_{24}$-aryloxy, $C_5$–$C_{25}$-arylalkyl, $C_5$–$C_{25}$-arylalkoxy or $NR^4R^5$ where $R^4$ and $R^5$ are each independently $C_1$–$C_{12}$-alkyl, $C_5$–$C_{14}$-aryl or $C_6$–$C_{15}$-arylalkyl, or $NR^4R^5$ as a whole is a 5- to 7-membered cyclic amino radical having a total of 4 to 12 carbon atoms, or $PR^1R^2$ as a whole is a 5- to 7-membered heterocyclic radical of the formula (V)

(V)

in which $Het^1$ and $Het^2$ are each independently absent, or are each oxygen or $NR^5$ where $R^5$ is $C_1$–$C_{12}$-alkyl, $C_5$–$C_{14}$-aryl or $C_6$–$C_{15}$-arylalkyl and K is an alkanediyl radical having 2 to 25 carbon atoms, a divalent arylalkyl radical having 5 to 15 carbon atoms, an arylene radical having a total of 5 to 14 carbon atoms or a 2,2'-(1,1'-bisarylene) radical having a total of 10 to 30 carbon atoms.

$R^1$ and $R^2$ are more preferably each independently $C_1$–$C_{12}$-alkyl, $C_5$–$C_{14}$-aryl, $C_6$–$C_{25}$-arylalkyl or radicals of the formula (V) in which $Het^1$ and $Het^2$ are each identically absent or are each independently oxygen or nitrogen and K is a $C_1$–$C_8$-alkylene radical or a 2,2'-(1,1'-bisphenylene) or 2,2'-(1,1'-bisnaphthylene) radical which are further substituted by up to two substituents per cycle selected from the group of fluorine, chlorine, $C_1$–$C_4$-alkyl and $C_1$–$C_4$-alkoxy.

$R^1$ and $R^2$ are even more preferably each independently and, still more preferably, each identically, methyl, ethyl, n-propyl, isopropyl, tert-butyl, cyclohexyl, benzyl, o-, m-, p-tolyl, 2,6-dimethylphenyl, 3,5-di-tert-butylphenyl, p-trifluoromethylphenyl, 3,5-bis(trifluoromethylphenyl), p-tert-butylphenyl, o-, m-, p-anisyl, 2,6-dimethoxyphenyl, o-, m-, p-dimethylaminophenyl, 2-, 3-, 4-pyridyl, 2-furanyl, 2-pyrrolyl or radicals of (IV) in which either $Het^1$ and $Het^2$ are each absent and K is a $C_1$–$C_8$-alkylene radical or $Het^1$-K-$Het^2$ as a whole is a 2,2-dioxy-(1,1-binaphthyl) radical or a 2,2'-dioxy-(1,1'-biphenyl) radical which is disubstituted at least in the 6,6'-positions, but has at most two substituents per cycle, and the substituents are selected from the group of fluorine, chlorine, $C_1$–$C_4$-alkyl and $C_1$–$C_4$-alkoxy.

$PR^1R^2$ is most preferably as a whole diisopropylphosphino, di-tert-butylphosphino, dicyclohexylphosphino, diphenylphosphino, bis(o-, m-, p-tolyl)phosphino, di-(3,5-bis(trifluoromethylphenyl)phosphino, di-(o-anisyl)phosphino, di-(2-pyridyl)phosphino, (R,R)-2,5-dimethylphospholano, or (S,S)-2,5-dimethylphospholano.

$A^1$ and $A^2$ are preferably each independently an ortho-phenylene radical of the formula (VI)

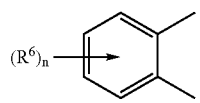

(VI)

in which n is 0, 1, 2, 3 or 4, preferably 0, 1 or 2, and more preferably 0 or 1, and $R^6$ is in each case independently selected from the group of fluorine, chlorine, bromine, iodine, nitro, free and protected formyl, $C_1$–$C_{12}$-alkyl, $C_1$–$C_{12}$-alkoxy, $C_1$–$C_{12}$-haloalkoxy, $C_1$–$C_{12}$-haloalkyl, $C_5$–$C_{14}$-aryl, $C_6$–$C_{15}$-arylalkyl or radicals of the formula (VII)

L-Q-T-W (VII)

in which, each independently,

L is absent or is $C_1$–$C_8$-alkylene or $C_2$–$C_8$-alkenylene and

Q is absent or is oxygen, sulphur or $NR^7$
where
$R^7$ is hydrogen, $C_1$–$C_8$-alkyl, $C_6$–$C_{15}$-arylalkyl or $C_5$–$C_{14}$-aryl and T is a carbonyl group and W is $R^8$, $OR^8$, $NHR^9$ or $N(R^9)_2$,
where
$R^8$ is $C_1$–$C_8$-alkyl, $C_5$–$C_{15}$-arylalkyl or $C_5$–$C_{14}$-aryl and $R^9$ is in each case independently $C_1$–$C_8$-alkyl, $C_5$–$C_{14}$-arylalkyl or $C_4$–$C_{15}$-aryl, or $N(R^9)_2$ together is a 5- or 6-membered cyclic amino radical, or a radical of the formulae (VIIIa–g)

L-W (VIIIa)

L-$SO_2$—W (VIIIb)

L-$NR^{12}SO_2R^{12}$ (VIIIc)

L-$SO_3Z$ (VIIId)

L-$PO_3Z_2$ (VIIIe)

L-COZ (VIIIf)

L-CN (VIIIg)

in which L, Q, W and $R^8$ are each as defined under the formula (VII) and Z is hydrogen or $M^1$ where $M^1$ is as defined under the definition of $R^7$.

$A^1$ and $A^2$ are more preferably each independently, even more preferably identically, an ortho-phenylene radical of the formula (VI) in which n is 0 or 1 and $R^6$ is in each case independently selected from the group of fluorine, chlorine, bromine, iodine, cyano, $C_1$–$C_4$-alkyl, $C_1$–$C_4$-alkoxy, di-($C_1$–$C_4$-alkyl)amino, ($C_1$–$C_4$-alkyl)amino, $C_1$–$C_4$-alkylthio, $CO_2M^1$, $CONH_2$, $SONH_2$, $SO_2N(C_1$–$C_4$-alkyl$)_2$, $SO_3M^1$ where $M^1$ is in each case lithium, sodium or potassium.

$A^1$ and $A^2$ are still more preferably identically an ortho-phenylene radical of the formula (VI) in which n is 0 or 1 and $R^6$ is selected from the group of fluorine, chlorine, cyano, methyl, ethyl, methoxy, ethoxy, methylthio, dimethylamino, $CONH_2$, $SO_2N$(methyl$)_2$ or $SO_2N$(ethyl$)_2$ where, when n=1, $R^6$ is still more preferably arranged in the para-position to E.

$A^1$ and $A^2$ are most preferably each identically ortho-phenylene.

$E^1$ is preferably a radical of the formula (IXa)

(IXa)

in which $R^{10}$ and $R^{11}$ are each independently hydrogen, cyano, fluorine, chlorine, bromine, iodine, $C_1$–$C_{18}$-alkyl, $C_4$–$C_{24}$-aryl, $C_5$–$C_{25}$-arylalkyl, $CO_2M$, $CONH_2$, $SO_2N(R^{12})_2$, $SO_3M^1$, where $R^{12}$ is in each case independently as defined above or is a radical of the formula (X), $T^2$-$Het^3$-$R^{13}$ (X)

in which $T^2$ is absent or is carbonyl, $Het^3$ is oxygen or $NR^{12}$ where $R^{12}$ is hydrogen, $C_1$–$C_{12}$-alkyl, $C_5$–$C_{14}$-aryl or $C_6$–$C_{15}$-arylalkyl and $R^{13}$ is $C_1$–$C_{18}$-alkyl, $C_5$–$C_{24}$-aryl or $C_5$–$C_{25}$-arylalkyl.

$E^2$ is preferably a radical of the formula (IXb)

in which $R^{14}$ and $R^{15}$ are each independently hydrogen, $C_1$–$C_{18}$-alkyl, $C_5$–$C_{24}$-aryl or $C_5$–$C_{25}$-arylalkyl.

E is preferably $E^1$.

$E^1$ is more preferably a radical of the formula (IXa) in which one of the two $R^{10}$ and $R^{11}$ radicals is hydrogen and the other radical is selected from the group of hydrogen, cyano, fluorine, $C_1$–$C_{12}$-alkyl, phenyl, $C_1$–$C_{18}$-alkoxy and $C_5$–$C_{15}$-arylalkoxy, where $C_1$–$C_{18}$-alkoxy and $C_5$–$C_{15}$-arylalkoxy are preferably chiral.

Very particular preference is given to one of the two $R^{10}$ and $R^{11}$ radicals being hydrogen and the other radical being selected from the group of hydrogen, cyano, fluorine, phenyl, methoxy and menthoxy, (−)-menthoxy being preferred among the 8 isomers.

The process according to the invention is especially suitable for preparing the following compounds:

10-cyano-5-diphenylphosphinyl-5H-dibenzo[a,d]cycloheptene ($^{CN}$tropp$^{Ph}$), 5-(2S,5S-2,5-dimethylphospholanyl)-5H-dibenzo[a,d]cycloheptene (S,S-tropphos$^{Me}$), 5-(2R,5R-2,5-dimethylphospholanyl)-5H-dibenzo[a,d]cycloheptene (R,R-tropphos$^{Me}$), (10-methoxy-5H-dibenzo[a,d]cyclohepten-5-yl)diphenylphosphine ($^{MeO}$tropp$^{Ph}$), (10-methoxy-5H-dibenzo[a,d]cyclohepten-5-yl)dicyclohexylphosphine ($^{MeO}$tropp$^{Cyc}$),

[(5S)-10-[(−)-menthyloxy]-5H-dibenzo[a,d]cyclohepten-5-yl]diphenylphosphine, (S-$^{menthyloxy}$tropp$^{Ph}$) and [(5R)-10-[(−)-menthyloxy]-5H-dibenzo[a,d]cyclohepten-5-yl]diphenylphosphine (R-$^{men-thyloxy}$tropp$^{Ph}$) are prepared.

In step a) of the process according to the invention, the compounds of the formula (II) are reacted with compounds of the formula (III) in the presence of acid or base to give compounds of the formula (IV).

The reaction may optionally and preferably be carried out in the presence of organic solvent, as long as the solvents are at least substantially inert towards the particular acid or base used.

Suitable organic solvents are, for example:

aliphatic or aromatic, optionally halogenated hydrocarbons, for example various benzines, benzene, toluene, xylene, chlorobenzene, dichlorobenzene, various petroleum ethers, hexane, cyclohexane, dichloromethane, chloroform, carbon tetrachloride; ethers such as diethyl ether, methyl tert-butyl ether, diisopropyl ether, dioxane, tetrahydrofluan or ethylene glycol dimethyl ether or ethylene glycol diethyl ether; amides such as N,N-dimethylformamide, N,N-dimethyl-acetamide, N-methylformanilide, N-methylpyrrolidone, N-methylcaprolactam or hexamethylphosphoramide; sulphoxides such as dimethyl sulphoxide, sulphones such as tetramethylenesulphone, alcohols such as methanol, ethanol, n- or isopropanol, ethylene glycol monomethyl ether, ethylene glycol monoethyl ether, diethylene glycol monomethyl ether, diethylene glycol monoethyl ether, or mixtures of such organic solvents. Preferred organic solvents are ethers.

Suitable bases are, for example: alkaline earth metal or alkali metal hydrides, hydroxides, amides, alkoxides or carbonates, for example sodium hydride, sodium amide, lithium diethylamide, sodium methoxide, sodium ethoxide, potassium tert-butoxide, sodium hydroxide, potassium hydroxide, sodium carbonate and potassium carbonate, organolithium compounds, for example n-butyllithium or methyllithium, tertiary amines such as trimethylamine, triethylamine, tributylamine, trioctylamine, diisopropylethylamine, tetramethylguanidine, N,N-dimethylaniline, diazabicyclooctane (DABCO), diazabicyclononene (DBN) or diazabicycloundecene (DBU), piperidine and N-methylpiperidine and N-heteroaromatics, for example pyridine and N,N-dimethylaminopyridine.

Preferred bases are tertiary amines in which the radicals are each independently selected from the group of $C_1$–$C_{12}$-alkyl, for example trimethylamine, triethylamine, tributylamine and trioctylamine, and even greater preference is given to those tertiary amines which are liquid under the selected reaction conditions.

Preference is given to using acids for the process according to the invention.

Preferred acids are those which, based on an aqueous reference scale and 25° C., have a pKa value of 5.5 or less.

These are, for example, ($C_1$–$C_{12}$-alkyl)carboxylic acids, ($C_1$–$C_{12}$-haloalkyl)carboxylic acids, ($C_1$–$C_{12}$-haloalkyl)sulphonic acids, ($C_1$–$C_{12}$-alkyl)sulphonic acids, ($C_5$–$C_{14}$-aryl) sulphonic acids, hydrogen chloride, hydrogen bromide and hydrogen iodide, optionally dissolved in acetic acid, sulphuric acid, ortho- and polyphosphoric acids, hexafluorophosphoric acid and tetrafluoroboric acid.

Particular preference is given to ($C_1$–$C_{12}$-haloalkyl)carboxylic acids, in particular trifluoroacetic acid.

The reaction in step a) may be carried out, for example, at a temperature of −20° C. to 100° C., preferably at 0 to 80° C. and more preferably at ambient temperature.

The reaction pressure may be, for example, 0.5 to 100 bar, preferably 0.9 to 5 bar. Particular preference is given to ambient temperature.

For example and with preference, acid and compound of the formula (II) may be initially charged in an organic solvent and the compound of the formula (III) added.

In step b) of the process according to the invention, compounds of the formula (IV) are reduced.

Preference is given to effecting this reduction in the presence of hydrosilicon compounds. Preferred hydrosilicon compounds are polymethylhydrosiloxane (PHMS) or those of the formula (XI)

in which p is 0, 1, 2 or 3 and $R^{16}$ is in each case independently $C_1$–$C_8$-alkyl, $C_1$–$C_8$-alkoxy, $C_5$–$C_{14}$-aryl or chlorine, and even greater preference is given to trichlorosilane.

Preference is given to carrying out the reaction in the presence of solvent. Preferred solvents are aliphatic or aromatic, optionally halogenated hydrocarbons, for example various benzines, benzene, toluene, xylene, chlorobenzene, dichlorobenzene, various petroleum ethers, hexane, cyclohexane, dichloromethane, chloroform, carbon tetrachloride or mixtures thereof.

The reaction in step b) may be carried out, for example, at a temperature of 20° C. to 200° C., preferably 50 to 150° C. and more preferably at 100 to 150° C.

The reaction pressure may be, for example, 0.5 to 100 bar, preferably 0.9 to 5 bar. Particular preference is given to ambient pressure.

For example and with preference, the hydrosilicon compound and the compound of the formula (IV) may be initially charged at room temperature in an organic solvent and the reaction mixture then heated at ambient pressure to the boiling point of the solvent used.

In a further aspect, the invention relates to compounds of the formula (IVa) and also to a process for preparing compounds of the formula (IVa)

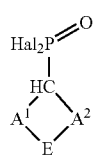
(IVa)

in which $A^1$, $A^2$ and E are each as defined under the formula (I) including their areas of preference and Hal is in each case independently chlorine, bromine or iodine, preferably identically chlorine or bromine and more preferably identically chlorine, which is characterized in that compounds of the formula (II) as defined above are reacted in the presence of acid or base with compounds of the formula (IIIa)

PHal$_3$ (IIIa)

in which

Hal is in each case independently chlorine, bromine or iodine, preferably identically chlorine or bromine and more preferably identically chlorine.

All specifications made above for step a) apply here correspondingly.

Compounds of the formula (IVa) include:
5-dichlorooxyphosphoryl-5H-dibenzo[a,d]cycloheptene (troppo$^{Cl}$) and 5-dibromooxyphosphoryl-5H-dibenzo[a,d]cycloheptene (troppo$^{Br}$)

The compounds of the formula (IVa) are valuable intermediates and can be prepared, for example, by reacting with compounds of the formula (XII)

$R^{1/2}$-M (XII)

in which $R^1$ and $R^2$ are each as defined above including the areas of preference specified and M, in the case that $R^1$ or $R^2$ are to be bonded to the phosphorus atom via an oxygen atom, is hydrogen or 1/n equivalent of a metal or of a metal fragment having the valency n, and, in the case that $R^1$ or $R^2$ are to be bonded to the phosphorus atom via a nitrogen atom, is hydrogen, and, in the case that $R^1$ or $R^2$ are to be bonded to the phosphorus atom via a carbon atom, is 1/n equivalent of a metal or of a metal fragment having the valency n, the same also applying in a similar manner to radicals in which $R^1R^2$ as a whole is a divalent radical.

Preferred metals are alkali metal, alkaline earth metal or transition metals, for example lithium, potassium, sodium, magnesium, zinc or copper, and particular preference is given to lithium, magnesium and zinc:

Preferred metal fragments are monovalent halometal fragments, for example MgCl, MgBr, MgI, ZnCl, ZnBr and ZnI.

The compounds obtainable in this way which can be encompassed by the formula (IV) may then likewise be reduced in step b) to the free phosphines of the formula (I).

The compounds of the formula (I) which can be prepared in accordance with the invention are especially suitable as ligands for metals and for use in catalytic processes. Preferred catalytic processes are hydrogenations and hydrosilylations.

The compounds of the formula (IV) and (IVa) which can be prepared in accordance with the invention are especially suitable for use in a process for preparing ligands and catalysts.

The advantage of the present invention is that, using compounds which are easy to obtain and can be handled without risk, olefin-phosphorus compounds can be prepared in high yields.

The invention is further illustrated but is not intended to be limited by the following examples in which all parts and percentages are by weight unless otherwise specified.

EXAMPLES

Example 1

Synthesis of
5-diphenyloxophosphoranyldibenzo[a,d]cycloheptene
(troppo$^{ph}$)

In a 500 ml reaction vessel, 14 g of dibenzo[a,d]cyclohepten-5-ol (0.067 mol) are dissolved in 250 ml of THF. Subsequently, 11.1 ml of trifluoroacetic acid (0.144 mol) are added and subsequently 25.84 ml of dichlorophenylphosphine (0.144 mol) are added. A white precipitate forms. The reaction mixture is left to stir at room temperature for 30 minutes. Subsequently, the reaction mixture is neutralized using K$_2$CO$_3$ solution. The organic phase is removed, and the residues are washed three times with 100 ml of [lacuna] and once with 100 ml of Et$_2$O. The combined organic phases are dried over Na$_2$SO$_4$ and the solvent is subsequently removed. The residue is recrystallized from CH$_2$Cl$_2$/n-hexane and 18.38 g (70% yield) of a colourless crystalline solid are obtained.

$^{31}$P NMR (CDCl$_3$, 121 MHz): δ 29.28

$^1$H NMR (CDCl$_3$, 300 MHz): δ 4.93 [d, $^2$J(PH)=16 Hz, 1H, PCH$_{benzyl}$), 6.56 (s, 2H, H$_{olefin}$), 7.59–7.17 (m, 19H, H$_{arom}$).

Example 2

Synthesis of
5-diphenylphosphinyldibenzo[a,d]cycloheptene
(tropp$^{ph}$)

In a 100 ml reaction vessel with reflux condenser, 1 g of troppo$^{Ph}$ from Example 1 (2.7 mmol) is dissolved in 50 ml of toluene and admixed with 2.6 ml of HSiCl$_3$. The reaction mixture is heated to 120° C. for 8 h. The progress of the reaction is monitored by $^{31}$P NMR spectroscopy. The reaction mixture is cooled to 0° C. and 30 ml of a deoxygenated 20% NaOH solution are added dropwise. Subsequently, the organic phase is separated and dried over Na$_2$SO$_4$. After the solvent has been evaporated off under reduced pressure, 0.88 g (93% yield) of pure tropp$^{Ph}$ is obtained.

$^{31}$P NMR (CDCl$_3$, 101 MHz): δ −14.2 (s).

$^1$H NMR (CDCl$_3$, 250 MHz): δ 4.93 (d, $^2$J(PH)=5.5 Hz, 2H, PCH$_{benzyl}$), 7.20–6.87 (m, 15H, H$_{arom}$), 7.25 (s, 2H, H$_{olefin}$), 7.44–7.41 (m, 3H, H$_{arom}$)

Example 3

Synthesis of 5-diphenyloxophosphoranyl-10-phenyldibenzo[a,d]cycloheptene ($^{ph}$troppo$^{ph}$)

520 mg of 5-hydroxy-10-phenyldibenzo[a,d]cycloheptene (1.8 mmol) in 15 ml of $CH_2Cl_2$ are admixed with 0.15 ml of $CF_3COOH$ (1.13 mmol). The solution becomes red and 0.33 ml of chlorodiphenylphosphine (2.26 mmol) is added. Another 0.15 ml of $CF_3COOH$ (1.13 mmol) is then added to the reaction mixture. This gives a clear yellow solution which is stirred at room temperature for 2 h. Subsequently, 20 ml of $Na_2CO_3$ (18% in $H_2O$) are added. The organic phase is removed and the aqueous extracted 3× with 20 ml of $CH_2Cl_2$ each time. The combined organic phases are dried over $MgSO_4$ and the solvent is subsequently evaporated. This gives a white foam which contains spectroscopically pure product (660 mg, 80%).

$^{31}$P NMR: 27.3 ppm—$^1$H NMR: 5.15 (d, $^2$JPH=13 Hz, 1 H, CHP), 6.50 (s, 1 H, =CH), 7.0–7.9 (m, 23 H, $H_{arom}$).

Example 4

Synthesis of 5-diphenylphosphinyl-10-phenyldibenzo[a,d]cycloheptene ($^{ph}$tropp$^{ph}$)

660 mg of 5-diphenyloxophosphoranyl-10-phenyldibenzo[a,d]cycloheptene (1.44 mmol) are dissolved in 20 ml of toluene and 1.8 ml of $SiHCl_3$ are added. The reaction mixture is heated to 120° C. under reflux for 10 h. After cooling, 25 ml of 20% deoxygenated KOH are added with cooling. The organic phase is removed and dried over $MgSO_4$. After removing all volatile components, a yellow foam is obtained which fluoresces intensely under UV light.

$^{31}$P NMR ($CDCl_3$): −13.1 ppm—$^1$H NMR: 4.99 (d, $^2J_{PH}$=6 Hz, 1H, CHP), 6.90 (d, $J_{PH}$=6 Hz, 1 H, =CH), 7.0–7.53 (m, 23 H, Harom).

Example 5

Synthesis of 5-diallyloxophosphoranyldibenzo[a,d]cycloheptene (troppo$^{allyl}$)

To a solution of 50 mg of 5-dichlorooxophosphoranyldibenzo[a,d]cycloheptene, which has been prepared in a similar manner to Example 1 (0.2 mmol) in 1 ml of THF is added 0.2 ml of allylmagnesium chloride (2 M in THF). The reaction mixture becomes red-brown. After 1 h at room temperature, the reaction mixture is admixed with aqueous ammonium chloride solution and the organic phase is removed. The aqueous phase is extracted with $CH_2Cl_2$ and the combined organic phases are dried over $MgSO_4$. After removing the solvent, 5-diallyloxophosphoranyldibenzo[a,d]cycloheptene is obtained as a colourless solid.

$^{31}$P NMR ($CDCl_3$): 45.8 ppm—$^1$H NMR: 2.44 (dd, $^2J_{PH}$=14.5 Hz, $^3J_{HH}$=7.6 Hz, 2 H, $CH_2$), 4.49 (d, $^2J_{PH}$=16.2 Hz, 1 H, CHP).

Example 6

Synthesis of 5-diallylphosphinyldibenzo[a,d]cycloheptene (tropp$^{allyl}$)

In a similar manner to Example 4, 5-diallyloxophosphoranyldibenzo[a,d]cycloheptene is reduced quantitatively using $HSiCl_3$ in toluene within 2 h to 5-diallylphosphinyldibenzo[a,d]cycloheptene.

$^{31}$P NMR ($CDCl_3$): −28.1 ppm.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims

What is claimed is:

1. Process for preparing compounds of the formula (I)

(I)

in which

R$^1$ and R$^2$ are each independently a monovalent radical which in each case has 1 to 30 carbon atoms or PR$^1$R$^2$ as a whole is a 5- to 9-membered heterocyclic radical which contains a total of 2 to 50 carbon atoms and optionally contains up to three further heteroatoms which are selected from the group of oxygen and nitrogen, and A$^1$ and A$^2$ are each independently a substituted or unsubstituted ortho-arylene radical and E is E$^1$ or E$^2$ where E$^1$ is an unsubstituted, monosubstituted or disubstituted vicinal cis-alkenediyl radical and E$^2$ is a vicinal alkanediyl radical in which the two yl carbon atoms each bear one or two hydrogen atoms, comprising in a step a), reacting compounds of the formula (II)

(II)

in which A$^1$, A$^2$ and E are each as defined above with compounds of the formula (III)

R$^1$R$^2$P-Hal (III)

in which R$^1$ and R$^2$ are each as defined above and Hal$^1$ is chlorine, bromine or iodine, in the presence of acid or base, to form compounds of the formula (IV)

(IV)

in which A$^1$, A$^2$, E, R$^1$ and R$^2$ are each as defined above and in a step b), reducing the compounds of the formula (IV) to compounds of the formula (I).

2. Process according to claim 1, characterized in that R$^1$ and R$^2$ are each independently $C_1$–$C_{18}$-alkyl, $C_3$–$C_{12}$-alkenyl, $C_1$–$C_{18}$-perfluoroalkyl, $C_1$–$C_{18}$-perfluoroalkoxy, $C_1$–$C_{18}$-alkoxy, $C_5$–$C_{24}$-aryl, $C_5$–$C_{24}$-aryloxy, $C_5$–$C_{25}$-arylalkyl, $C_5$–$C_{25}$-arylalkoxy or $NR^4R^5$ where $R^4$ and $R^5$ are each independently $C_1$–$C_{12}$-alkyl, $C_5$–$C_{14}$-aryl or $C_6$–$C_{15}$-arylalkyl, or $NR^4R^5$ as a whole is a 5- to 7-membered cyclic amino radical having a total of 4 to 12 carbon atoms, or $PR^1R^2$ as a whole is a 5- to 7-membered heterocyclic radical of the formula (V)

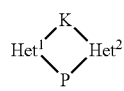 (V)

in which

Het$^1$ and Het$^2$ are each independently absent, or are each oxygen or $NR^5$ where $R^5$ is $C_1$–$C_{12}$-alkyl, $C_5$–$C_{14}$-aryl or $C_6$–$C_{15}$-arylalkyl and K is an alkanediyl radical having 2 to 25 carbon atoms, a divalent arylalkyl radical having 5 to 15 carbon atoms, an arylene radical having a total of 5 to 14 carbon atoms or a 2,2'-(1,1'-bisarylene) radical having a total of 10 to 30 carbon atoms.

3. Process according to claim 1, characterized in that $A^1$ and $A^2$ are each independently an ortho-phenylene radical of the formula (VI)

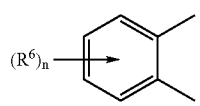 (VI)

in which n is 0, 1, 2, 3 or 4, preferably 0, 1 or 2, and $R^6$ is in each case independently selected from the group of fluorine, chlorine, bromine, iodine, nitro, free and protected formyl, $C_1$–$C_{12}$-alkyl, $C_1$–$C_{12}$-alkoxy, $C_1$–$C_{12}$-haloalkoxy, $C_1$–$C_{12}$-haloalkyl, $C_5$–$C_{14}$-aryl, $C_6$–$C_{15}$-arylalkyl or radicals of the formula (VII)

L-Q-T-W (VII)

in which, each independently,

L is absent or is $C_1$–$C_8$-alkylene or $C_2$–$C_8$-alkenylene and

Q is absent or is oxygen, sulphur or $NR^7$ where $R^7$ is hydrogen, $C_1$–$C_8$-alkyl, $C_6$–$C_{15}$-arylalkyl or $C_5$–$C_{14}$-aryl and T is a carbonyl-group and W is $R^8$, $OR^8$, $NHR^9$ or $N(R^9)_2$, where $R^8$ is $C_1$–$C_8$-alkyl, $C_5$–$C_{15}$-arylalkyl or $C_5$–$C_{14}$-aryl and $R^9$ is in each case independently $C_1$–$C_8$-alkyl, $C_5$–$C_{14}$-arylalkyl or $C_4$–$C_{15}$-aryl, or $N(R^9)_2$ together is a 5- or 6-membered cycloamino radical, or a radical of the formulae (VIIIa–g)

L-W (VIIIa)

L-SO$_2$-W (VIIIb)

L-NR$^{12}$SO$_2$R$^{12}$ (VIIIc)

L-SO$_3$Z (VIIId)

L-PO$_3$Z$_2$ (VIIIe)

L-COZ (VIIIf)

L-CN (VIIIg)

in which L, Q, W and $R^8$ are each as defined under the formula (VII) and Z is hydrogen or $M^1$ where $M^1$ is as defined under the definition of $R^7$.

4. Process according to claim 1, characterized in that E is a radical of the formulae (IXa) or (IXb) where, in formula (IXa)

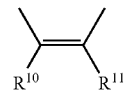 (IXa)

$R^{10}$ and $R^{11}$ are each independently hydrogen, cyano, fluorine, chlorine, bromine, iodine, $C_1$–$C_{18}$-alkyl, $C_4$–$C_{24}$-aryl, $C_5$–$C_{25}$-arylalkyl, CO$_2$M, CONH$_2$, SO$_2$N(R$^{12}$)$_2$, SO$_3$M$^1$, where $R^{12}$ is in each case independently as defined above or is a radical of the formula (X), T$^2$-Het$^3$-R$^{13}$ (X)

in which

T$^2$ is absent or is carbonyl,

Het$^3$ is oxygen or $NR^{12}$ where $R^{12}$ is hydrogen, $C_1$–$C_{12}$-alkyl, $C_5$–$C_{14}$-aryl or $C_6$–$C_{15}$-arylalkyl and $R^{13}$ is $C_1$–$C_{18}$-alkyl, $C_5$–$C_{24}$-aryl or $C_5$–$C_{25}$-arylalkyl, and, in formula (IXb),

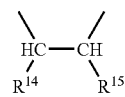 (IXb)

$R^{14}$ and $R^{15}$ are each independently hydrogen, $C_1$–$C_{18}$-alkyl, $C_5$–$C_{24}$-aryl or $C_5$–$C_{25}$-arylalkyl.

5. Process according to at least one of claims 1 to 4, characterized in that 10-cyano-5-diphenylphosphinyl-5H-dibenzo[a,d]cycloheptene ($^{CN}$tropp$^{Ph}$) 5-(2S,5S-2,5-dimethylphospholanyl)-5H-dibenzo[a,d]cycloheptene (S,S-tropphos$^{Me}$)

5-(2R,5R-2,5-dimethylphospholanyl)-5H-dibenzo[a,d]cycloheptene (R,R-tropphos$^{Me}$)

(10-methoxy-5H-dibenzo[a,d]cyclohepten-5-yl)diphenylphosphine ($^{MeO}$tropp$^{Ph}$)

(10-methoxy-5H-dibenzo[a,d]cyclohepten-5-yl)dicyclohexylphosphine ($^{MeO}$tropp$^{Cyc}$)

[(5S)-10-[(−)-menthyloxy]-5H-dibenzo[a,d]cyclohepten-5-yl]diphenylphosphine, (S-$^{menthyloxy}$tropp$^{Ph}$) and [(5R)-10-[(−)-menthyloxy]-5H-dibenzo[a,d]cyclohepten-5-yl]-diphenylphosphine (R-$^{menthyloxy}$tropp$^{Ph}$) are prepared.

6. Process according to claim 1, characterized in that acids are used for step a).

7. Process according to claim 1, characterized in that the acids used are those which, based on an aqueous reference scale and 25° C., have a pKa value of 5.5 or less.

8. Process according to claim 1, characterized in that step a) is carried out at a temperature of −20° C. to 100° C.

9. Process according to claim 1, characterized in that stereoisomer mixtures of compounds of the formula (IV), are separated before carrying out step b).

10. Process according to at least one of claims 1 to 9, characterized in that at least one of the $R^1$, $R^2$, $A^1$, $A^2$ and E radicals in the compounds of the formula (IV) is converted to another $R^1$, $R^2$, $A^1$, $A^2$ and E radical.

11. Process according to claim 1, characterized in that the reduction in step b) is carried out in the presence of hydrosilicon compounds.

12. Process according to claim 1, characterized in that the reduction in step b) is carried out at a temperature of 20° C. to 200° C.

13. Process according to claim 1, characterized in that the resulting compounds are reduced to the free phosphines in a further step.

14. Compounds of the formula (IVa)

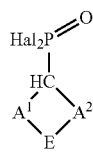

(IVa)

in which $A^1$, $A^2$ and E are each as defined in claim 1.

15. 5-Dichlorooxyphosphoryl-5H-dibenzo[a,d]cycloheptene (troppo$^{Cl}$) and 5-dibromooxyphosphoryl-5H-dibenzo[a,d]cycloheptene (troppo$^{Br}$).

16. Process for preparing compounds of the formula (IVa)

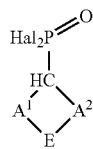

(IVa)

in which $A^1$, $A^2$ and E are each as defined in claim 1 and Hal is in each case chlorine, bromine or iodine, comprising reacting
compounds of the formula (II) as defined in claim 1 in the presence of acid or base with compounds of the formula (IIIa)

PHal$_3$     (IIIa)

in which
Hal is in each case independently chlorine, bromine or iodine.

17. Process according to claim 16, characterized in that the compounds of the formula (IVa) are also reacted with compounds of the formula (XII)

$R^{1/2}$-M     (XII)

in which $R^1$ and $R^2$ are each as defined in claim 1, and M, in the case that
$R^1$ or $R^2$ are to be bonded to the phosphorus atom via an oxygen atom, is hydrogen or 1/n equivalent of a metal or of a metal fragment having the valency n, and, in the case that
$R^1$ or $R^2$ are to be bonded to the phosphorus atom via a nitrogen atom, is hydrogen, and, in the case that
$R^1$ or $R^2$ are to be bonded to the phosphorus atom via a carbon atom, is 1/n equivalent of a metal or of a metal fragment having the valency n,
the same also applying in a similar manner to radicals in which $R^1R^2$ as a whole is a divalent radical.

18. Process according to claim 17, characterized in that the resulting compounds are reduced to the free phosphines in a further step.

19. A process for preparing ligand for metals or conducting catalytic processes comprising providing the compounds of claim 14.

20. The process of claim 19, characterized in that the catalytic processes are hydrogenations and hydrosilylations.

* * * * *